United States Patent [19]                [11] Patent Number:     5,242,928
Mederski et al.                                [45] Date of Patent:   Sep. 7, 1993

[54] IMIDAZOPYRIDINES

[75] Inventors: Werner Mederski, Erzhausen; Dieter Dorsch, Ober-Ramstadt; Norbert Beier, Reinheim; Pierre Schelling, Mühltal; Ingeborg Lues, Darmstadt; Klaus-Otto Minck, Ober-Ramstadt, all of Fed. Rep. of Germany

[73] Assignee: Merck Patent Gesellschaft Mit Beschränkter Haftung, Darmstadt, Fed. Rep. of Germany

[21] Appl. No.: 991,888

[22] Filed: Dec. 17, 1992

[30] Foreign Application Priority Data

Dec. 18, 1991 [DE] Fed. Rep. of Germany ....... 4141788

[51] Int. Cl.$^5$ ................. A61K 31/435; C07D 471/04
[52] U.S. Cl. ................................ 514/303; 544/238; 544/333; 544/405; 546/118
[58] Field of Search .................... 546/118; 514/303

[56] References Cited

U.S. PATENT DOCUMENTS 4,880,804  11/1989  Carini et al. ............... 514/234.5
5,036,048   7/1991  Watkins ....................... 514/16

FOREIGN PATENT DOCUMENTS 0400974  12/1990  European Pat. Off.
91/14367 10/1991  PCT Int'l Appl.

OTHER PUBLICATIONS

Chiu et al., The Journal of Pharmacology and Experimental Therapeutics, vol. 250, No. 3, pp. 867–874 (May 22, 1989).
Wong et al., The Journal of Pharmacology and Experimental Therapeutics, vol. 252, No. 2, pp. 719–725 (Oct. 26, 1989).

Primary Examiner—Bernard Dentz
Attorney, Agent, or Firm—Millen, White, Zelano & Branigan

[57] ABSTRACT

Novel imidazopyridine derivatives of formula I:

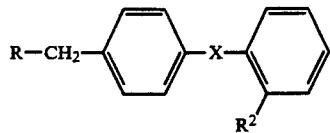

wherein
R is

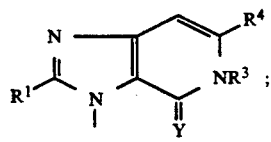

$R^1$ is A, alkenyl or alkynyl each having up to 6 C atoms,
$R^2$ is H, COOH, COOA, CN, NO$_2$, NHCOR$^5$, NHSO$_2$R$^5$ or 1H-tetrazol-5-yl,
$R^3$ is R$^5$—CO—alkyl, Ar—CO—alkyl, Het—CO—alkyl or Het-alkyl each having 1-6 C atoms in the alkyl moiety,
$R^4$ is H or Hal,
$R^5$ is alkyl having 1-6 C atoms, wherein one or more H atoms can also be replaced with F,
X is absent or is —NH—CO—, —CO—NH—, —O—CH(COOH)—, —NH—CH(COOH)—, —NA—CH(COOH)—, —CH=C(COOH)—, —CH=C(CN)— OR —CH=C(1H-tetrazol-t-yl)—,
Y is O or S,
A is alkyl having 1-6 C atoms,
Ar is unsubstituted phenyl or phenyl monosubstituted by R$^5$, OR$^5$, COOH, COOA, CN, NO$_2$, NH$_2$, NHCOR$^5$, NHSO$_2$R$^5$ or 1H-tetrazol-5-yl,
Het is a five- or six-membered heteroaromatic radical having 1 to 3 N, O and/or S atoms, which can also be fused with a benzene or pyridine ring, and
Hal is F, Cl, Br or I, and their salts, exhibit antagonistic properties towards angiotensin II and can be used for the treatment of hypertension, aldosteronism, cardiac insufficiency and increased intraocular pressure, and of disorders of the central nervous system.

24 Claims, No Drawings

IMIDAZOPYRIDINES

SUMMARY OF THE INVENTION

The invention relates to novel imidazopyridine derivatives of formula I:

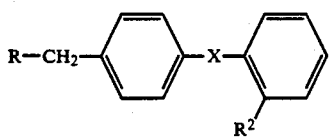

I wherein
R is

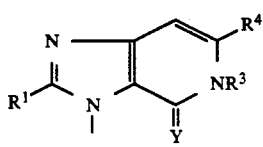

$R^1$ is A, alkenyl or alkynyl each having up to 6 C atoms,
$R^2$ is H, COOH, COOA, CN, $NO_2$, $NHCOR^5$, $NHSO_2R^5$ or 1H-tetrazol-5-yl,
$R^3$ is $R^5$—CO—alkyl, Ar—CO—alkyl, Het—CO—alkyl or Het-alkyl each having 1-6 C atoms in the alkyl moiety,
$R^4$ is H or Hal,
$R^5$ is alkyl having 1-6 C atoms, wherein one or more H atoms can also be replaced with F,
X is absent or is —NH—CO—, —CO—NH—, —O—CH(COOH)—, —NH—CH(COOH)—, —NA—CH(COOH)—, —CH=C(COOH)—, —CH=C(CN)— or —CH=C(1H-tetrazol-t-yl)—,
Y is O or S,
A is alkyl having 1-6 C atoms,
Ar is an unsubstituted phenyl group or a phenyl group monosubstituted by $R^5$, $OR^5$, COOH, COOA, CN, $NO_2$, $NH_2$, $NHCOR^5$, $NHSO_2R^5$ or 1H-tetrazol-5-yl,
Het is a five- or six-membered heteroaromatic radical having I to 3 N, O and/or S atoms, which can also be fused with a benzene or pyridine ring, and Hal is F, Cl, Br or I, and their salts.

Similar compounds are known from European patent application A2-0 400 974.

An object of the invention is to provide novel compounds with valuable properties, especially compounds which can be used for the preparation of drugs.

Upon further study of the specification and appended claims, further objects and advantages of this invention will become apparent to those skilled in the art.

It has been found that the compounds of formula I and their salts possess very valuable pharmacological properties coupled with a good tolerance. In particular, they exhibit antagonistic properties toward angiotensin II and can therefore be used for the treatment of angiotensin II-dependent hypertension, aldosteronism, cardiac insufficiency and increased intraocular pressure, and of disorders of the central nervous system.

These effects can be determined by conventional in vitro or in vivo methods such as, for example, those described in U.S. Pat. No. 4,880,804, U.S. Pat. No. 5,036,048 and international patent application 91/14367 and also by A.T. Chiu et al., J. Pharmacol. Exp. Therap. 250, 867–874. (1989), and by P.C. Wong et al., ibid. 252, 719–725 (1990; in vivo, on rats).

The compounds of formula I can be used as pharmaceutical active ingredients in human and veterinary medicine, especially for the prophylaxis and/or therapy of cardia, circulatory and vascular diseases, in particular of hypertonia, cardiac insufficiency and hyperaldosteronism, furthermore of hypertrophy and hyperplasy of the blood vessels and the heart, angina pectoris, cardiac infarction, haemorrhagic stroke, restenosis after angioplasty or by-pass surgery, arteriosclerosis, ocular hypertension, glaucoma, macular degeneration, hyperuricaemia, disturbances of the renal functions such as renal failure, diabetic complications such as nephropathia diabetica or retinopathia diabetica, psoriasis, angiotensin II-induced disturbances in female sexual organs, cognitive disorders, e.g., dementia, amnesia, disturbances of the function of memory, states of fear, depressions and/or epilepsy.

The invention relates to the compounds of formula I and their salts and to a process for the preparation of these compounds and their salt, characterized in that (a) a compound of formula II:

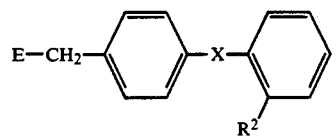

II wherein
E is Cl, Br, I, a free OH group or an OH group which has been functionally modified to acquire reactivity, and
$R^2$ and X are as defined above for formula I, is reacted with a compound of formula III:

H—R  III wherein
R is as defined above for formula I,
or
(b) a compound of formula IV:

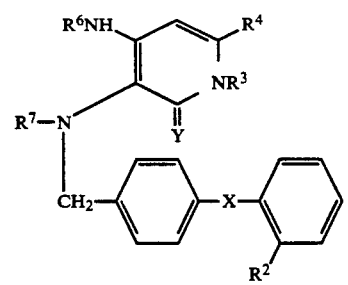

IV wherein
$R^6$ is $R^1$—CO or H,
$R^7$ is H (if $R^6$ is $R^1$—CO) or $R^1$—CO (if $R^6$ is H), and
$R^1$, $R^2$, $R^3$, $R^4$, X and Y are as defined above for formula I, is treated with a cyclizing agent,
or
(c) to prepare a compound of formula I wherein X is —NHCO— or —CO—NH—, a compound of formula V:

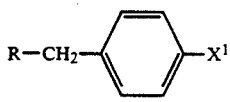

wherein
X¹ is NH₂ or COOH, and
R is as defined above for formula I,
or a reactive derivative of this compound, is reacted with a compound of formula VI:

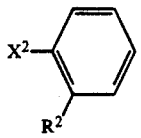

wherein
X² is COOH (if X¹ is NH₂) or NH₂ (if X¹ is COOH), and
R² is as defined above for formula I,
or with a reactive derivative of this compound, or
(d) a compound of formula VII:

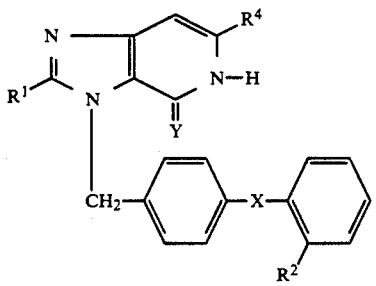

wherein
R¹, R², R⁴, X and Y are as defined above for formula I, is reacted with a compound of formula VIII:

E—R³    VIII wherein
R³ and E are as defined above for formulae I and II, respectively,
or in that a compound of formula I is freed from one of its functional derivatives by treatment with a solvolyzing or hydrogenolyzing agent, and/or in that one or more radicals R and/or R² in a compound of formula I are converted to one or more other radicals R and/or R², and/or a base or acid of formula I is converted to one of its salts.

Above and below, unless expressly indicated otherwise, the radicals or parameters R, R¹ to R⁷, X, Y, A, Hal, E, X¹ and X² are as defined in formulae I to VI.

In the above formulae, A has 1-6, preferably 1, 2, 3 or 4 C atoms. A is preferably methyl, or else ethyl, propyl, isopropyl, butyl, isobutyl, sec-butyl or tertbutyl, or else pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl- 1-methylpropyl, 1-ethyl-2-methylpropyl or 1,1,2-trimethylpropyl. Alkenyl is preferably vinyl, prop-1-enyl, prop-2-enyl or but-1-enyl, or else pent-1-enyl or hex-1-enyl. Alkynyl is preferably ethynyl, prop-1-ynyl or prop-2-ynyl, or else but-1-ynyl, pent-1-ynyl or hex-1-ynyl.

Hal is preferably F, Cl or Br, or else I.

R is a radical derived from 3H-imidazo[4,5-c]-pyridine ("3H-IP") or, more precisely, 2-R¹-4-(thi)oxo-5-R³-6-R⁴-4,5-dihydro-3H-imidazo[4,5-c]pyridin-3-yl.

Ar is preferably phenyl, o-, m- or p-tolyl, o-, m- or p-ethylphenyl, o-, m- or p-trifluoromethylphenyl, o-, m- or p-methoxyphenyl, o-, m- or p-ethoxyphenyl, o, m- or p-difluoromethoxyphenyl, o-, m- or p-trifluoromethoxyphenyl, o-, m- or p-carboxyphenyl, o-, m- or p-methoxycarbonylphenyl, o-, m- or p-ethoxycarbonylphenyl, o-, m- or p-cyanophenyl, o-, m- or p-nitrophenyl, o-, m- or p-aminophenyl, o-, m- or p-acetamidophenyl, o-, m- or p-trifluoroacetamidophenyl, o-, m- or p-methylsulfonaminophenyl, o-, m- or p-trifluoromethylsulfonamidophenyl or o-, m- or p-(1H-tetrazol-5-yl)phenyl.

Het is preferably furan-2- or -3-yl, thien-2- or -3-yl, pyrrol-1-, -2- or -3-yl, imidazol-1-, -2-, -4- or -5-yl, pyrazol-1-, 3-, -4- or -5-yl, oxazol-2-, -4- or -5-yl, isoxazol-3-, -4- or -5-yl, thiazol-2-, -4- or -5-yl, isothiazol-3-, 4- or -5-yl, pyridin-2-, -3- or -4-yl or pyrimidin-2-, -4-, -5- or -6-yl, or else preferably 1,2,3-triazol-1-, -4- or -5-yl, 1,2,4-triazol-1-, -3- or -5-yl, 1,2,3-oxadiazol-4- or -5-yl, 1,2,4-oxadiazol-3- or -5-yl, 1,3,4-thiadiazol-2- or -5- yl, 1,2,4-thiadiazol-3- or -5-yl, 2,1,5-thiadiazol-3- or -4-yl, pyridazin-3- or -4-yl, pyrazinyl, benzofuran- 2-, -3-, -4-, -5-, -6- or -7-yl, benzothien-2-, -3-, -4-, -5-, -6- or -7-yl, indol-1-, -2-, -3-, -4-, -5-, -6- or -7-yl, isoindol-1-, -2-, -3-, -4-, -5-, -6- or -7-yl, benzimidazol-1-, -2-, -4- or -5-yl, benzopyrazol-1-, -3-, -4-, -5-, -6- or -7-yl, benzoxazol-2-, -4, -5-, -6- or -7-yl, benzisoxazol-3-, -4-, -5-, -6- or -7-yl, benzthiazol-2-, -4-, -5-, -6- . or -7-yl, benzisothiazol-2-, -4-, -5-, -6- or -7-yl, benz-2,1,3-oxadiazol-4-, -5-, -6- or -7-yl, quinol-2-, -3-, -4-, -5-, -6-, -7- or -8-yl, isoquinol-1-, -3-, -4-, -5-, -6-, -7- or -8-yl, cinnolin-3-, -4-, -5-, -6-, -7- or -8-yl, quinazol-2-, -4-, -5-, -6-, -7- or -8-yl, 1H-imidazo[4,5-b]pyridin-1-, -2-, -5-, -6- or -7-yl, 3H-imidazo[4,5-b]pyridin-2-, -3-, -5-, -6- or -7-yl, 1H-imidazo[4,5-c]pyridin 1-, -2-, -4-, -6- or -7-yl or 3H-imidazo[4,5-c]pyridin-2-, -3-, -4-, -6- or -7-yl.

The term "Het" also includes the homologous radicals in which the heteroaromatic ring is substituted by one or more, preferably 1 or 2 groups A, preferably methyl and/or ethyl groups, for example 3-, 4- or 5-methylfuran-2-yl, 2-, 4- or 5-methylfuran-3-yl, 2,4-dimethylfuran-3-yl, 3-, 4- or 5-methylthien-2-yl, 3-methyl-5-tert-butylthien-2-yl, 2-, 4- or 5-methylthien-3-yl, 2- or 3-methylpyrrol-1-yl, 1-, 3-, 4- or 5-methylpyrrol-2-yl, 3,5-dimethyl-4-ethylpyrrol-2-yl, 2-, 4- or 5-methylimidazol-1-yl, 4-methylpyrazol-5-yl, 4- or 5-methylisoxazol-3-yl, 3- or 5-methylisoxazol-4-yl, 3- or 4-methylisoxazol-5-yl, 3,4-dimethylisoxazol-5-yl, 4- or 5-methylthiazol-2-yl, 4- or 5-ethylthiazol-2-yl, 2- or 5-methylthiazol-4-yl, 2- or 4-methylthiazol-5-yl, 2,4-dimethylthiazol-5-yl, 3-, 4-, 5- or 6-methylpyridin-2-yl, 2-, 4-, 5- or 6-methylpyridin-3-yl, 2- or 3-methylpyridin-4-yl, 4-methylpyrimidin-2 yl, 4,6-dimethylpyrimidin-2-yl, 2-, 5- or 6-methylpyrimidin-4-yl, 2,6-dimethylpyrimidin-4-yl, 3-, 4-, 5-, 6- or 7-methylbenzofuran-2-yl, 2-ethylbenzofuran 3-yl, 3-, 4-, 5-, 6- or 7-methylbenzothien-2-yl, 3-ethylbenzothien-2-yl, 1-, 2-, 4-, 5-, 6- or 7-methylindol-3-yl, 1-methylbenzimidazol-5- or -6-yl or 1-ethylbenzimidazol-5- or -6-yl.

Preferably, the radical R¹ is linear and is A or alkenyl each having 3-6 C atoms, especially butyl, or else propyl, pentyl, hexyl, allyl or prop-1-enyl, or else but-1- enyl, pent-1-enyl, hex-1-enyl, prop-1-ynyl, but-1-ynyl, pent-1-ynyl or hex-1-ynyl.

The radical $R^2$ is preferably 1H-tetrazol-5-yl, or else preferably COOH, COOCH$_3$, COOC$_2$H$_5$, CN or NHSO$_2$CF$_3$.

The "alkyl" moiety in the radical $R^3$ is preferably —CH$_2$—.

Accordingly the radical $R^3$ is preferably $R^5$—CO—CH$_2$—, Ar—CO—CH$_2$—, Het—CO—CH$_2$— or Het—CH$_2$—.

Some preferred radicals $R^3$ are 2-oxopropyl, 2-oxobutyl, 3-methyl-2-oxobutyl, 3,3-dimethyl-2-oxobutyl, 3,3,3-trifluoro-2-oxopropyl, 3,3,4,4,4-pentafluoro-2-oxobutyl, phenacyl (=2-oxo-2-phenylethyl), o-, m- or p- methylphenacyl, o-, m- or p-ethylphenacyl, o-, m- or p- trifluoromethylphenacyl, o-, m- or p-methoxyphenacyl, o-, m- or p-ethoxyphenacyl, o-, m- or p-difluoromethoxyphenacyl, o-, m- or p-trifluoromethoxyphenacyl, o-, m- or p carboxyphenacyl, o-, m- or p-methoxycarbonylphenacyl, o-, m- or p-ethoxycarbonylphenacyl, o-, m- or p-cyanophenacyl, o-, m- or p-nitrophenacyl, o-, m- or p-aminophenacyl, o-, m- or p-acetamidophenacyl, o-, m- or p- trifluoroacetamidophenacyl, o-, m or p-methylsulfonamidophenacyl, o-, m- or p-trifluoromethylsulfonamidophenacyl, o-, m- or p-(1H-tetrazol-5-yl)phenacyl, furan-2-oylmethyl, then-2-oylmethyl, picolinoylmethyl, nicotinoylmethyl, isonicotinoylmethyl, pyrazinecarbonylmethyl, pyrimidine-2-, -4-, -5- or -6-carbonylmethyl, pyridazine-3- or -4-carbonylmethyl, benzofuran-2-, -3-, -4-, -5-, -6- or -7-carbonylmethyl, benzothiophene-2-, 5 -3-, -4-, -5-, -6- or -7- carbonylmethyl, indole-2-, -3-, -4-, -5-, -6- or -7- carbonylmethyl, furan-2- or -3-ylmethyl, thien-2- or -3-ylmethyl, isoxazol-5-ylmethyl, 5-methylisoxazol-3-ylmethyl, pyridin-2-, -3- or -4-ylmethyl, pyrazinylmethyl, pyrimidin-2-, -4-., -5- or -6-ylmethyl, pyridazin-3- or -4-ylmethyl, benzofuran-2-, -3-, -4-, -5-, -6- or -7-ylmethyl, benzothien-2-, -3-, -4-, -5-, -6- or -7-ylmethyl or indol-2-, -3-, -4-, -5-, -6- or -7- ylmethyl. Of the substituted phenacyl groups, those substituted in the p-position are preferred.

The radical $R^4$ is preferably H, or else F, Cl, Br or I.

Preferably, the radical $R^5$ contains 1, 2 or 3 C atoms and is methyl, ethyl, trifluoromethyl, pentafluoroethyl, 2,2,2-trifluoroethyl or 3,3,3-trifluoropropyl. If a compound of formula I contains two radicals $R^5$, they can be identical to or different from one another.

Preferably, the radical X is absent or is —NHCO— or —CO—NH—.

The radical Y is preferably O, or else S.

The compounds of formula I can possess one or more chiral centers and can therefore exist in different forms (optically active or optically inactive). Formula I includes all these forms.

Accordingly the invention relates especially to those compounds of formula I in which at least one of said radicals has one of the preferred meanings indicated above. Some preferred groups of compounds can be expressed by the following partial formulae Ia to Ii, which correspond to formula I and wherein the radicals not described more precisely are as defined in formula I, except that:
in Ia: X is absent;
in Ib: X is —NH—CO—;
in Ic: X is —CO—NH—;
in Id: X is —O—CH(COOH)—;
in Ie: X is —NH—CH(COOH)—;
in If: X is —NA—CH(COOH)—;
in Ig: X is —CH=C(COOH)—;
in Ih: X is —CH=C(CN)—;
in Ii: X is —CH=C(1H-tetrazol-5-yl)-.

Compounds of formula Ia are particularly preferred. The following are also preferred: compounds of formulae Ik and Iak to Iik, which correspond to the compounds of formulae I and Ia to Ii, except that in addition Y is an O atom; compounds of formulae Il, Ial to Ikl and Iakl to Iikl, which correspond to formulae I, Ia to Ik and Iak to Iik, except that in addition $R^4$ is H; compounds of formulae Im, Iam to Ilm, Ialm to Iklm and Iaklm to Iiklm, which correspond to formulae I, Ia to Il, Ial to Ikl and Iakl to Iikl, except that in addition $R^2$ is CN or 1H-tetrazol-5-yl.

Among these, preferred compounds are those in which $R^1$ is A or alkenyl each having 3-6 C atoms.

Other preferred groups of compounds have formula I and the other formulae given above, except that the radical $R^3$ is
(a) $R^5$—CO—CH$_2$—,
(b) Ar—CO—CH$_2$—,
(c) Het—CO—CH$_2$—,
(d) Het—CH$_2$— or
(e) p aminophenacyl.

A small selected group of preferred compounds has formula I wherein
R is a 2-butyl-4,5-dihydro-4-oxo-5-$R^3$-3H-imidazo[4,5-c]pyridin-3-yl radical,
$R^2$ is tetrazol-5-yl,
$R^3$ is 3,3-dimethyl-2-oxobutyl, phenacyl, 2-(benzofuran-2-oxoethyl or thien-2-ylmethyl, and
X is absent.

The compounds of formula I and also the starting materials for their preparation are moreover prepared by methods known per se, such as those described in the literature (for example in the standard works like Houben-Weyl, Methoden der organischen Chemie (Methods of Organic Chemistry), Georg-Thieme-Verlag, Stuttgart, but especially in European patent application A2-0 430 709 and U.S. Pat. No. 4 880 804), under conditions which are known and suitable for said reactions, it also--being possible to make use of variants known per se, which are not mentioned in greater detail here.

If desired, the starting materials can also be formed in situ, so that they are not isolated from the reaction mixture but immediately reacted further to give the compounds of formula I.

The compounds of formula I can preferably be obtained by reacting compounds of formula II with compounds of formula III. Particularly the biphenyl derivatives of formula I (wherein X is absent) are readily obtainable in this way.

In the compounds of formula II, E is preferably Cl, Br, I or an OH group which has been functionally modified to acquire reactivity, such as alkylsulfonyloxy having 1-6 C atoms (preferably methylsulfonyloxy) or arylsulfonyloxy having 6-10 C atoms (preferably phenyl- or p-tolyl-sulfonyloxy).

The reaction of II with III is conveniently carried out by first converting III to a salt by treatment with a base, for example with an alkali metal alcoholate such as CH$_3$ONa or potassium tert-butylate in an alcohol such as CH$_3$OH, or with an alkali metal hydride such as NaH, or with an alkali metal alcoholate in dimethylformamide (DMF), and then reacting said salt with II in an inert solvent, for example an amide such as DMF or dimethylacetamide, or a sulfoxide such as dimethyl sulfoxide (DMSO), conveniently at temperatures of between −20 and 100°, preferably of between 10 and 30°. Other suitable bases are alkali metal carbonates such as $Na_2CO_3$ or $K_2CO_3$, or alkali metal hydrogen carbonates such as $NaHCO_3$ or $KHCO_3$.

The compounds of formula I can also be obtained by the cyclization of compounds of formula IV. This cyclization is conveniently carried out by heating with polyphosphoric acid, acetic acid or diglyme to temperatures of between about 80° and 180°, preferably of between 120 and 160°.

Acid amides of formula I (X = —NH—CO— or —CONH—) can also be obtained by reacting compounds of formula V (or reactive derivatives thereof) with compounds of formula VI (or reactive derivatives thereof).

Suitable reactive derivatives of the carboxylic acids of formulae V and VI ($X^1$ or $X^2$ = COOH) are advantageously the corresponding chlorides, bromides or anhydrides. The reaction is conveniently carried out in the presence of an inert solvent, for example a halogenated hydrocarbon such as methylene chloride, chloroform, trichloroethene or 1,2-dichloroethane, or an ether such as tetrahydrofuran (THF) or dioxane, at temperatures of between 0° and 150°, preferably of between 20° and 80°. If acid halides are reacted, it is recommended to add a base, for example a tertiary amine such as triethylamine, pyridine or 4-dimethylaminopyridine.

The compounds of formula I can also be obtained by reacting a compound of formula VII (corresponding to formula I but with H in place of $R^3$) with a compound of formula VIII. This reaction is preferably carried out in an acid amide such as DMF, N-methylpyrrolidone, 1,3-dimethyl- 2 -oxohexahydropyrimidine or hexamethylphosphorotriamide, an alcohol such as methanol or tert-butanol, an ether such as THF, or a halogenated hydrocarbon such as methylene chloride, or mixtures thereof, as the solvent, and/or in the presence of an alkali metal alcoholate such as sodium methylate or potassium tert-butylate, an alkali metal hydride such as sodium or potassium hydride, an alkali metal carbonate such as sodium or potassium carbonate, an alkali metal bicarbonate such as sodium or potassium bicarbonate, or a tertiary amine such as triethylamine or ethyldiisopropylamine, at temperatures of between about −30° and 200°, preferably of between 20° and 60°.

It is also possible to free a compound of formula I from one of its functional derivatives by solvolysis (for example hydrolysis) or hydrogenolysis.

Thus carboxylic acids of formula I wherein X is —O—CH(COOH), —NH—CH(COOH), —NA—CH-(COOH) or —CH═C(COOH) can be obtained by the saponification of corresponding alkyl esters, for example with NaOH or KOH in aqueous solution, with or without the addition of an inert organic solvent such as methanol, ethanol, THF or dioxane, at temperatures of between 0° and 100°, or by the hydrogenolysis of corresponding benzyl esters, for example on Pd-on-charcoal at pressures of between 1 and 200 bar and at temperatures of between 0° and 100°, in one of the inert solvents indicated.

It is also possible, using one of the methods indicated, to prepare a compound which has formula I but in which a tetrazol-5-yl group is replaced with a 1H(or 2H)-tetrazol-5-yl group functionally modified in the 1-position (or 2-position) (protected by a protecting group). Examples of suitable protecting groups are: triphenylmethyl, which can be cleaved with HCl or formic acid in an inert solvent or solvent mixture, for example ether/methylene chloride/methanol; 2-cyanoethyl, which can be cleaved with NaOH in water/THF; and p-nitrobenzyl, which can be cleaved with $H_2$/Raney nickel in (compare European patent application A2-0 291 969).

Some of the starting materials, especially those of formulae II, VI and VIII, are known. If they are not known, they can be prepared by known methods analogously to known substances. Compounds of formula III (Y = O) can be obtained for example by reacting carboxylic acids of the formula $R^1$—COOH with compounds of formula IX:

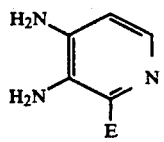

in the presence of polyphosphoric acid; the group E (preferably Cl) is hydrolyzed in the process and compounds of formula III in which $R^3$ = H are formed initially; these are then reacted with compounds of formula VIII.

Compounds of formula IV can be obtained for example by reacting compounds of formula X:

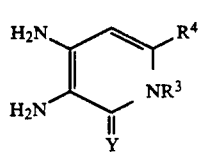

wherein, however, one of the amino groups is protected by - an amino-protecting group (for example benzyl, A—O— CO— or benzyloxycarbonyl), with compounds of formula II and subsequently cleaving the protecting group and reacting the products with acids of the formula $R^1$—COOH or functional derivatives thereof; they are not normally isolated; but are formed in situ in the last-mentioned reaction Compounds of formula V can be prepared by reacting III with benzyl chlorides of the formula $ClCH_2$—p—$C_6H_4$—$X^3$ (wherein $X^3$ is a protected $NH_2$ or COOH group) and subsequently cleaving the protecting group.

Compounds of formula VII can be obtained for example by reacting compounds of formula III, carrying an H atom in place of $R^3$, with compounds of formula II.

It is also possible to convert one compound of formula I to another compound of formula I by converting one or more of the radicals R and/or $R^2$ to other radicals R and/or $R^2$, for example by reducing nitro groups to amino groups (for example by hydrogenation on Raney nickel or Pd-on-charcoal in an inert solvent such as methanol or ethanol), and/or functionally modifying free amino and/or hydroxyl groups, and/or freeing functionally modified amino and/or hydroxyl groups by solvolysis or hydrogenolysis, and/or hydrolyzing nitrile groups to COOH groups, or converting nitrile groups to tetrazolyl groups with hydrazoic acid derivatives, for example sodium azide in N-methylpyrrolidone or trimethyltin azide in toluene.

Thus, for example, free amino groups can be acylated in conventional manner with an acid chloride or anhydride, or alkylated with an unsubstituted or substituted alkyl halide, conveniently in an inert solvent such as methylene chloride or THF, and/or in the presence of a base such as triethylamine or pyridine, at temperatures of between $-60°$ and $+30°$.

If desired, a functionally modified amino and/or hydroxyl group in a compound of formula I can be freed by solvolysis or hydrogenolysis using conventional methods. Thus, for example, a compound of formula I containing an $NHCOR^5$ or COOA group can be converted to the corresponding compound of formula I containing an $NH_2$ or HOOC group instead. COOA groups can be saponified for example with NaOH or KOH in water, water/THF or water/dioxane, at temperatures of between $0°$ and $100°$.

The reaction of nitriles of formula I (for example those in which $R^2 = CN$) with hydrazoic acid derivatives leads to tetrazoles of formula I (for example in which $R^2 =$ 1H-tetrazol-5-yl). It is preferable to use trialkyltin azides such as trimethyltin azide, in an inert solvent, for example an aromatic hydrocarbon such as toluene, at temperatures of between $20°$ and $150°$, preferably of between $80°$ and $140°$, or sodium azide in N-methylpyrrolidone at temperatures of between about $100°$ and $200°$.

A base of formula I can be converted with an acid to the corresponding acid addition salt. Possible acids for this reaction are especially those which yield physiologically acceptable salts. Thus it is possible to use inorganic acids, for example sulfuric acid, nitric acid, hydrohalic acids such as hydrochloric acid or hydrobromic acid, phosphorus acids such as orthophosphoric acid, and sulfamic acid, as well as organic acids, especially aliphatic, alicyclic, araliphatic, aromatic or heterocyclic monobasic or polybasic carboxylic, sulfonic or sulfuric acids, or example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethane-sulfonic acid, ethanedisulfonic acid, 2-hydroxyethanesulfonic acid, benzenesulfonic acid, p-toluenesulfonic acid, naphthalene-monosulfonic and disulfonic acids and laurylsulfuric acid. Salts with physiologically unacceptable acids, for example picrates, can be used for isolating and/or purifying the compounds of formula I.

On the other hand, compounds of formula I containing COOH or tetrazolyl groups can be converted with bases (for example sodium or potassium hydroxide or carbonate) to the corresponding metal salts, especially alkali metal or alkaline earth metal salts, or to the corresponding ammonium salts. The potassium salts of the tetrazolyl derivatives are particularly preferred.

The novel compounds of formula I and their physiologically acceptable salts can used for the manufacture of pharmaceutical preparations by incorporation into a suitable dosage form together with at least one excipient or adjunct and, if desired, together with one or more other active ingredients. The resulting formulations can be used as drugs in human or veterinary medicine. Possible excipients are organic or inorganic substances which are suitable for enteral (for example oral or rectal) or parenteral administration or for administration in the form of an inhalation spray, and which do not react with the novel compounds, examples being water, vegetable oils, benzyl alcohols, polyethylene glycols, glycerol triacetate and other fatty acid glycerides, gelatin, soya lecithin, carbohydrates such as lactose or starch, magnesium stearate, talc and cellulose. Tablets, coated tablets, capsules, syrups, juices or drops, in particular, are used for oral administration; lacquered tablets and capsules with coatings or shells resistant to gastric juices are of special interest. Suppositories are used for rectal administration and solutions, preferably oily or aqueous solutions, as well as suspensions, emulsions or implants, are used for parenteral administration. For administration as inhalation sprays, it is possible to use sprays containing the active ingredient either dissolved or suspended in a propellant mixture (for example fluorochlorohydrocarbons). It is convenient here to use the active ingredient in micronized form, it being possible for one or more additional physiologically compatible solvents, for example ethanol, to be present. Inhalation solutions can be administered with the aid of conventional inhalers. The novel compounds can also be lyophilized and the resulting lyophilizates used for example for the manufacture of injectable preparations. The indicated formulations can be sterilized and/or can contain adjuncts such as preservatives, stabilizers and/or wetting agents, emulsifiers, salts for influencing the osmotic pressure, buffer substances and colors and/or flavorings. If desired, they can also contain one or more other active ingredients, for example one or more vitamins, diaretics or antiphlogistics.

The substances according to the invention are normally administered analogously to other known, commercially available preparations (e,g., Enalapril or Captopril), but in particular analogously to the compounds described in U.S. Pat. No. 4,880,804, preferably in doses of about 1 mg-1 g, especially 50–500 mg per dosage unit. The daily dose is preferably about 0.1–50 mg/kg, especially 1–100 mg/kg of body weight. However, the particular dose for each individual patient depends on a very wide variety of factors, for example on the efficacy of the particular compound used, age, body weight, general state of health, sex, diet, time and mode and severity of the particular disease to which the therapy is applied. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application German P 41 41 788.7, filed Dec. 18, 1991, are hereby incorporated by reference.

Above and below, all temperatures are given in °C. In the following Examples, "Conventional working-up" means: water is added if necessary, the pH is adjusted to between 2 and 10 if necessary, depending on the constitution of the end product, extraction is carried out with ethyl acetate or methylene chloride and the organic phase is separated off, dried over sodium sulfate, evaporated and purified by chromatography on silica gel and/or by crystallization.

IP = imidazo[4,5-c]pyridine.

EXAMPLES

Example 1

(a) A solution of 0.23 g of Na in 20 ml of methanol is added dropwise over 15 minutes to a solution of 2.71 g of 2-butyl-5-(furan-2-ylmethyl)-4,5-dihydro-4-oxo-3H-IP [obtainable by condensation of valeric acid with 3,4-diamino-2-chloropyridine, in the presence of polyphosphoric acid, to give 2-butyl- 4,5-dihydro-4-oxo-1(or 3)H-IP, reaction with benzyl bromide in methanol, in the presence of CH$_3$ONa, to give 3-benzyl-2-butyl-4,5-dihydro-4-oxo-3H-IP, reaction with furan-2-ylmethyl chloride in DMF, in the presence of potassium tertbutylate, to give 3- benzyl-2-butyl-5-(furan-2-ylmethyl)-4,5-dihydro-4-oxo-3H-IP, and hydrogenolytic cleavage of the benzyl group] in 75 ml of methanol. The mixture is stirred for a further 30 minutes at 20° and evaporated, the residue is dissolved in 20 ml of DMF, and a solution of 3.05 g of methyl 4,-bromomethylbiphenyl-2-carboxylate (IIa) in 10 ml of DMF is added dropwise at 0°, with stirring. The mixture is stirred for 16 hours at 20°, evaporated, worked up in conventional manner and chromatographed on silica gel to give 2-butyl-5-(furan2-ylmethyl)- 4,5-dihydro-3-(2,-methoxycarbonylbiphenyl4-ylmethyl)-4-oxo-3H-IP.

(b) A mixture of 1 g of the methyl ester obtained according to (a), 12 ml of 2 N aqueous NaOH solution and 48 ml of methanol is boiled for 2 hours and then evaporated. The residue is worked up in conventional manner (aqueous hydrochloric acid to pH 3/methylene chloride) to give 2-butyl-5-(furan-2-ylmethyl)-4,5,-dihydro-3-(2.-carboxybiphenyl-4-ylmethyl)-4-oxo-3H-IP.

Example 2

2-Butyl-3-[p-(1-cyano-2-phenylvinyl)benzyl]-4,5-dihydro-4-oxo-5-(thien-2-ylmethyl)-3H-IP is obtained analogously to Example 1 from 2.87 g of 2-butyl-4,5-dihydro-4-oxo-5-(thien-2-ylmethyl)-3H-IP and 2.98 g of 3-p-bromomethylphenyl-2-phenylacrylonitrile [m.p. 178°; obtainable by condensation of p-tolylaldehyde with phenylacetonitrile in ethanol, in the presence of C$_2$H$_5$ONa, to give 2-phenyl-3-p-tolylacrylonitrile (m.p. 61°), and bromination with N-bromosuccinimide in methylene chloride].

Example 3

A mixture of 1.02 g of valeric acid, 4.55 g of 4-amino-1,2-dihydro-2-oxo-3-[2,-(1H-tetrazol-5-yl)biphenyl-4-ylmethylamino]-1-(thien 2-ylmethyl)pyridine [obtainable by reaction of 3-amino-4 benzylamino-1,2-dihydro-2-oxo-1-(thien-2-ylmethyl)pyridine with 4-bromomethyl-2,-cyanobiphenyl to give 4-benzylamino-3-(2'-cyanobiphenyl-4-ylmethylamino)-1,2-dihydro-2 oxo-1-(thien-2 ylmethyl)pyridine, reaction with trimethyltin azide to give 4-benzylamino-1,2-dihydro-2-oxo-3-[2,-(1H-tetrazol-5-yl)biphenyl-4-ylmethylamino]-1-(thien-2-ylmethyl)pyridine, and hydrogenolytic cleavage of the benzyl group] and 50 g of polyphosphoric acid is heated for 5 hours at 140°. 4-Amino-1,2-dihydro-2-oxo-3-[N-(2'(1H-tetrazol-5-yl)biphenyl-4-ylmethyl-N-valeryl-amino]-1-(thien-2-ylmethyl)pyridine and 1,2-dihydro-2-oxo-3-[2'-(1H-tetrazol-5-yl)biphenyl-4-ylmethylamino]-1-(thien-2-ylmethyl)-4-valerylaminopyridine are formed in situ as intermediates. The mixture is cooled, poured on to ice, rendered alkaline with sodium hydroxide solution and worked up in conventional manner to give 2-butyl-4,5-dihydro-4-oxo-3-[2,-(1H-tetrazol-5-yl)biphenyl-4-ylmethyl]-5-(thien-2-ylmethyl)-3H-IP, m.p. 145°.

Example 4

A mixture of 1.1 g of 3-p-aminobenzyl-2-butyl4,5-dihydro-4-oxo-5-(thien-2-ylmethyl)-3H-IP [obtainable by reaction of 2-butyl-4,5-dihydro-4-oxo-5-(thien-2-ylmethyl)-3H-IP with p-nitrobenzyl bromide to give 2-butyl-4,5-dihydro-3-p-nitrobenzyl-4-oxo-5-(thien-2-ylmethyl)-3H-IP, and subsequent hydrogenation], 0.6 g of phthalic anhydride and 40 ml of CHCl$_3$ is stirred for 16 hours at 20°. The 2-butyl-3-[4-(o-carboxybenzamido)-benzyl]-4,5-dihydro-4-oxo-5-(thien-2-ylmethyl)-3H-IP which has precipitated out is filtered off.

Example 5

A mixture of 3.92 g of 3-p-aminobenzyl-2-butyl-4,5-dihydro-4-oxo-5-(thien-2-ylmethyl)-3H-IP, 3 ml of triethylamine, 0.5 g of 4-dimethylaminopyridine and 120 ml of methylene chloride is cooled to 5° and a solution of 2.88 g of o-trifluoromethanesulfonamidobenzoyl chloride in 20 ml of methylene chloride is added dropwise. The mixture is stirred for a further 16 hours at 20°, evaporated and worked up in conventional manner to give 2-butyl-4,5-dihydro-4-oxo-5-(thien-2-ylmethyl)-3-[4-(o-trifluoromethanesulfonamidobenzamido)benzyl]-3H-IP.

Example 6

A mixture of 4.88 g of 2-butyl-3-p-carboxybenzyl4,5-dihydro-5-p-nitrophenacyl-4-oxo-3H-IP, 12 g of thionyl chloride and 35 ml of CHCl$_3$ is boiled for 6 hours and evaporated. The crude acid chloride obtained is freed of thionyl chloride residues by dissolution in toluene several times, followed each time by evaporation, and is dissolved in 80 ml of THF. This solution is added dropwise to a solution of 1.7 g of anthranilic acid and 0.8 g of NaOH in 100 ml of water and the mixture is stirred for 24 hours and acidified to pH 5 with hydrochloric acid. 2-Butyl-3-[p-(2-carboxyanilinocarbonyl)benzyl]-4,5-dihydro-5-p-nitrophenacyl-4-oxo-3H-IP is obtained after conventional working-up.

Example 7

(a) 1.25 g of potassium tert-butylate are added at 20° to a solution of 3.1 g of 2-butyl-3-(2'-cyanobiphenyl-4-ylmethyl)-4,5-dihydro-4-oxo-3H-IP (m.p. 179°–180°; obtainable from 2-butyl-4,5-dihydro-4-oxo-1(or 3)H-IP with 4'-bromomethyl-2-cyanobiphenyl in DMF, in the presence of K$_2$CO$_3$) in 35 ml of DMF, with stirring. After stirring for 45 minutes, a solution of 2.65 g of thien2-ylmethyl chloride in 25 ml of DMF is added dropwise. The mixture is stirred for a further 16 hours at 20° and worked up in conventional manner to give 2-butyl-3-(2'-cyanobiphenyl-4-ylmethyl)-4,5-dihydro-4-oxo-5-(thien-2-ylmethyl)-3H-IP, m.p. 63°–64°.

The following 2-butyl-3-(2, cyanobiphenyl-4-ylmethyl)-4,5-dihydro-4-oxo-5-R$^3$-3H-IP are obtained analogously:

| | |
|---|---|
| with furan-2-ylmethyl chloride: | -5-(furan-2-ylmethyl)- |
| with isoxazol-5-ylmethyl bromide: | -5-(isoxazol-5-ylmethyl)- |
| with 5-methylisoxazol-3-yl-methyl bromide: | -5-(5-methylisoxazol-3-yl-methyl)- |
| with pyridin-2-ylmethyl chloride: | -5-(pyridin-2-ylmethyl)- |

| -continued | |
|---|---|
| with pyridin-3-ylmethyl chloride: | -5-(pyridin-3-ylmethyl)- |
| with pyridin-4-ylmethyl chloride: | -5-(pyridin-4-ylmethyl)- |
| with 2-(furan-2-yl)-2-oxo-ethyl bromide: | -5-(furan-2-oylmethyl)- |
| with 2-(thien-2-yl)-2-oxo-ethyl bromide: | -5-(then-2-oylmethyl)- |
| with bromo- or chloro-acetone: | -5-(2-oxopropyl)-, m.p. 57° |
| with phenacyl chloride or bromide: | -5-phenacyl-, m.p. 70° |
| with o-methoxyphenacyl chloride: | -5-o-methoxyphenacyl-, m.p. 93° |
| with 1-bromobutan-2-one: | -5-(2-oxobutyl)- |
| with 1-bromo-3-methylbutan-2-one: | -5-(3-methyl-2-oxobutyl)- |
| with 1-bromo-3,3-dimethyl-butan-2-one: | -5-(3,3-dimethyl-2-oxo-butyl)-, m.p. 156° |
| with o-nitrophenacyl chloride: | -5-o-nitrophenacyl- |
| with m-nitrophenacyl chloride: | -5-m-nitrophenacyl- |
| with p-nitrophenacyl chloride: | -5-p-nitrophenacyl- |
| with 1-bromo-3,3,3-tri-fluoroacetone: | -5-(3,3,3-trifluoro-2-oxo-propyl)- |
| with 1-bromo-3,3,4,4,4-pentafluorobutan-2-one: | -5-(3,3,4,4,4-pentafluoro-2-oxobutyl)- |
| with 2-(pyridin-3-yl)-2-oxo-ethyl chloride: | -5-nicotinoylmethyl- |
| with p-difluoromethoxy-phenacyl chloride: | -5-p-difluoromethoxy-phenacyl- |
| with p-trifluoromethoxy-phenacyl chloride: | -5-p-trifluoromethoxy-phenacyl- |
| with p-cyanophenacyl chloride: | -5-p-cyanophenacyl- |
| with 2-(benzofuran-2-yl)-2-oxoethyl bromide: | -5-[2-(benzofuran-2-yl)-2-oxoethyl]-, m.p. 95°. |

(b) A mixture of 4.06 g of the compound obtained according to (a), 20.6 g of trimethyltin azide and 200 ml of toluene is boiled for 24 hours and then evaporated. The residue is taken up in 100 ml of methanolic HCl and the mixture is stirred for 2 hours at 20° and worked up in conventional manner (saturated NaCl solution/methylene chloride). Chromatography (ethyl acetate/hexane 80:20) gives 2-butyl-4,5-dihydro-4-oxo-3-[2'-1H-tetrazol-5-yl)-biphenyl-4-ylmethyl]-5-(thien-2-ylmethyl)-3H-IP, m.p. 145°.

The following 2-butyl-4,5-dihydro-4-oxo-3-[2'-(1Htetrazol-5-yl)biphenyl-4-ylmethyl]-5-R3-3H-IP are obtained analogously from the 2'-cyanobiphenylyl compounds indicated under (a):
-5-(furan-2-ylmethyl)-
5-(isoxazol-5-ylmethyl)-
5-(5-methylisoxazol-3-ylmethyl)-
5-(pyridin-2-ylmethyl)-
5-(pyridin-3-ylmethyl)-
5-(pyridin-4-ylmethyl)-
5-(furan-2-oylmethyl)-
5-(then-2-oylmethy)-
5-(2-oxopropyl)-, m.p. 154°
-5-phenacyl-, m.p. 189°
-5-o-methoxyphenacyl-, m.p. 133°
-5-(2-oxobutyl)-
5-(3-methyl-2-oxobutyl)-
5-(3,3dimethyl-2-oxobutyl)-, m.p. 203°
-5-o-nitrophenacyl-
5-m-nitrophenacyl-
5-p-nitrophenacyl-
5-(3,3,3-trifluoro-2-oxopropyl)-
5-(3,3,4,4,4-pentafluoro-2-oxobutyl)-
5-nicotinoylmethyl-
5-p-difluoromethoxyphenancyl-
5-p-trifluoromethoxyphenacyl-
5-p-cyanophenacyl-
5-[2-(benzofuran-2-yl)-2-oxoethyl]-; m.p. 194°.

Example 8

(a) 2-Butyl-4,5-dihydro-4-oxo-5-(thien-2-ylmethyl)-3-[2'-(2-triphenylmethyl-2H-tetrazolyl)biphenyl-4-ylmethyl]-3H-IP is obtained analogously to Example 7 from 2-butyl-4,5-dihydro-4-oxo-3-[2,-(2-triphenylmethyl-2H-tetrazol-5-yl)biphenyl-4-ylmethyl]- 3H-IP with thien-2-ylmethyl chloride.

The following 2-butyl-4,5-dihydro-4-oxo-3-[2'-(2-triphenylmethyl-2H-tetrazol-5-yl)biphenyl 4-ylmethyl]-5-R3-3H-IP are obtained analogously:
-5-(furan-2-ylmethyl)-
5-(isoxazol-5-ylmethyl)-
5-(5-methylisoxazol-3-ylmethyl)-
5-(pyridin-2-ylmethyl)-
5-(pyridin-3-ylmethyl)-
5-(pyridin-4-ylmethyl)-
5-(furan-2-oylmethyl)-
5-(then-2-oylmethyl)-
5-(2-oxopropyl)-
5-phenacyl-
5-o-methoxyphenacyl-
5-(2-oxobutyl)-
5-(3-methyl-2-oxobutyl)-
5-(3,3-dimethyl-2-oxobutyl)-
5-o-nitrophenacyl-
5-m-nitrophenacyl-
5-p-nitrophenacyl-
5-(3,3,3-trifluoro-2-oxopropyl)-
5-(3,3,4,4,4-pentafluoro-2-oxobutyl)-
5-nicotinoylmethyl-
5-p-difluoromethoxyphenacyl-
5-p-trifluoromethoxyphenacyl-
5-p-cyanophenacyl-
5-[2-(benzofuran-2-yl)-2-oxoethyl]-.

(b) The product obtained according to (a) (1 g) is dissolved in 60 ml of 4 N HCl in dioxane and the solution is stirred for 16 hours at 20°. It is evaporated and worked up in conventional manner to give 2-butyl-4,5-dihydro-4-oxo-3-[2,-(1H-tetrazol- 5-yl)biphenyl-4-ylmethyl]-5-(thien-2-ylmethyl)-3H- IP.

The 1H-tetrazol-5-yl compounds indicated in Example 7(b) are obtained analogously from the corresponding 2-triphenylmethyl-2H-tetrazol-5-yl compounds indicated under (a).

Example 9

5-(2-Benzoylethyl)-2-butyl-3-(p-2-cyano-2-phenyl-vinylbenzyl)-4,5-dihydro-4-oxo-3H-IP is obtained analogously to Example 7 from 2-butyl-3-(p-2-cyano-2-phenylvinylbenzyl)-4,5-dihydro-4-oxo-3H-IP (m.p. 160°; obtainable from 2-butyl-4,5-dihydro-4-oxo-1(or 3)H-IP and 3-p-bromomethylphenyl-2-phenylacrylonitrile) with 2-benzoyl-1-chloroethane.

Example 10

2-Butyl-3-[p-(α-carboxybenzyloxy)benzyl]-4,5-dihydro-4-oxo-5-phenacyl-3H-IP is obtained analogously to Example 1(b) by saponification of 2-butyl-4,5-dihydro-3-[p-(α-methoxycarbonylbenzyloxy)benzyl]-4-oxo-5-phenacyl-3H-IP (obtainable by reaction of 2-butyl-3-p-acetoxybenzyl-4,5-dihydro-4-oxo-3H-IP with phenacyl bromide to give the 5-phenacyl compound, hydrolysis to 2-butyl-4,5-dihydro-3-p-hydroxybenzyl-4-oxo-5-phenacyl-3H-IP, and etherification with methyl α-bromophenyl-acetate).

Example 11

A solution of 1 g of 2-butyl-4,5-dihydro-5-p-nitrophenacyl-4-oxo-3-[2'-(1H-tetrazol-5-yl)biphenyl-4-ylmethyl]-3H-IP in 20 ml of methanol is hydrogenated on 0.3 g of 5% Pd-on-charcoal at 20° and normal pressure until the calculated amount of Hz has been taken up. The catalyst is filtered off and the filtrate is evaporated to give 5-p-aminophenacyl-2-butyl-4,5-dihydro-4-oxo-3-[2,-(1H-tetrazol-5-yl)biphenyl-4-ylmethyl]-3H-IP.

The following 2-butyl-4,5-dihydro-4-oxo-3-[2'-(1H-tetrazol-5-yl)biphenyl-4-ylmethyl]-3H-IP are obtained analogously by hydrogenation of the corresponding nitro compounds given in Example 7(b):
5-o-aminophenacyl-
5-m-aminophenacyl-.

Example 12

A solution of 2.82 g of trifluoromethanesulfonic anhydride in 10 ml of methylene chloride is added dropwise at −50° to −60° to a solution of 5.5 g of 5-p-aminophenacyl-2-butyl-4,5-dihydro-4-oxo-3-[2,-(1H-tetrazol-5-yl)biphenyl-4-ylmethyl]-3H-IP and 1.01 g of triethylamine in 30 ml of methylene chloride. The mixture is left to warm up to 20°, poured into dilute acetic acid and worked up in conventional manner to give 2-butyl-4,5-dihydro-4 oxo-3-[2'(1H-tetrazolyl)biphenyl-4-ylmethyl]-5-p-trifluoromethanesulfonamidophenacyl-3H-IP.

The following 2-butyl-4,5-dihydro-4-oxo-3-[2'-(1H-tetrazolyl)biphenyl-4-ylmethyl]-3H-IP are obtained analogously by acylation of the amino compounds given in Example 11:
5-o-trifluoromethanesulfonamidophenacyl-
5-m-trifluoromethanesulfonamidophenacyl-.

The following Examples relate to pharmaceutical formulations containing active ingredients of formula I or their salts.

Example A: Tablets and coated tablets

Tablets of the following composition are produced by compression in conventional manner and, where required, are provided with a conventional sucrose-based coating:

| Active ingredient of formula I | 100 mg |
| Microcrystalline cellulose | 278.8 mg |
| Lactose | 110 mg |
| Maize starch | 11 mg |
| Magnesium stearate | 5 mg |
| Finely divided silicon dioxide | 0.2 mg |

Example B: Hard gelatin capsules

Conventional two-part hard gelatin capsules are each filled with

| Active ingredient of formula I | 100 mg |
| Lactose | 150 mg |
| Cellulose | 50 mg |
| Magnesium stearate | 6 mg |

Example C: Soft gelatin capsules

Conventional soft gelatin capsules are filled with a mixture of 50 mg of active ingredient and 250 mg of olive oil in each case.

Example D: Ampoules

A solution of 200 g of active ingredient in 2 kg of propane-1,2-diol is made up to 10 l with water and filled into ampoules so that each ampoule contains 20 mg of active ingredient.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An imidazopyridine compound of formula I:

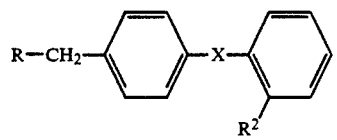

wherein
R is

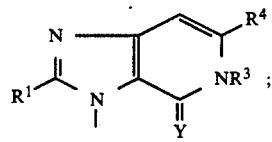

$R^1$ is A, alkenyl or alkynyl each having up to 6 C atoms;
$R^2$ is H, COOH, COOA, CN, $NO_2$, $NHCOR^5$, $NHSO_2R^5$ or 1H-tetrazol-5-yl;
$R^3$ is $R^5$—CO—alkyl, Ar—CO—alkyl, Het—CO—alkyl or Het-alkyl, in each case having 1–6 C atoms in the alkyl moiety;
$R^4$ is H or Hal;
$R^5$ is alkyl having 1–6 C atoms, wherein one or more H atoms can also be replaced with F;
X is absent or is —NH—CO—, —CO—NH—, —O—CH(COOH)—, —NH—CH(COOH)—, —NA—CH(COOH)—, —CH=C(COOH)—, —CH=(CN)— or —CSH=1H-tetrazol-t-yl)—;
Y is O or S;
A is alkyl having 1–6 C atoms;
Ar is unsubstituted phenyl or phenyl monosubstituted by $R^5$, $OR^5$, COOH, COOA, CN, $NO_2$, $NH_2$, $NHCOR^5$, $NHSO_2R^5$ or 1H-tetrazol-5-yl;
Het is a five- or six-membered heteroaromatic radical having 1 to 3 N, O and/or S atoms, which can also be fused with a benzene or pyridine ring; and
Hal is F, Cl, Br or I; or a physiologically acceptable salt thereof.

2. A compound according to claim 1, wherein said compound is:
(a) 2-butyl-4,5-dihydro-5-(3,3-dimethyl-2-oxobutyl)-4-oxo-3-[2'-(1H-tetrazol-5-yl)biphenyl-4-yl-methyl]-

3H-imidazo[4,5-c]pyridine or a physiologically acceptable salt thereof;

(b) 2-butyl-4,5-dihydro-4-oxo-5-phenacyl-3-[2'-(1H-tetrazol-5-yl)biphenyl-4-yl-methyl]-3H-imidazo-[4,5-c]pyridine or a physiologically acceptable salt thereof;

(c) 2-butyl-4,5-dihydro-4-oxo-3-[2'-(1H-tetrazol5-yl)biphenyl-4-yl-methyl]-5-(thien-2-yl-methyl)-3H-imidazo[4,5-c]pyridine or a physiologically acceptable salt thereof; or (d) 5-[benzofuran-2-yl)-2-oxoethyl]-2-butyl-4,5-dihydro-3-[2'-(1H-tetrazol-5-yl)biphenyl-4-ylmethyl]-4-oxo-3H-imidazo[4,5-c]pyridine or a physiologically acceptable salt thereof.

3. A compound according to claim 1, wherein X is absent.

4. A compound according to claim 1, wherein X is —NH—CO.

5. A compound according to claim 1, wherein X is —CO—NH—.

6. A compound according to claim 1, wherein X is —O—CH(COOH)—.

7. A compound according to claim 1, wherein X is —NH—CH(COOH)—.

8. A compound according to claim 1, wherein X is —NA—CH(COOH)—.

9. A compound according to claim 1, wherein X is —CH=C(COOH)—.

10. A compound according to claim 1, wherein X is —CH=C(CN)—.

11. A compound according to claim 1, wherein X is —CH=C(1H-tetrazol-5-yl)-.

12. A compound according to claim 1, wherein Y is O.

13. A compound according to claim 1, wherein $R^4$ is H.

14. A compound according to claim 1, wherein $R^2$ is CN or 1H-tetrazol-5-yl.

15. A compound according to claim 1, wherein $R^1$ is alkyl having 3-6 C atoms or alkenyl having 3-6 C atoms.

16. A compound according to claim 1, wherein $R^3$ is $R^5$—CO—CH$_2$—, Ar—CO—CH$_2$—, Het—CO—CH$_2$— or Het—CH$_2$—.

17. A compound according to claim 1, wherein $R^3$ is p-aminophenacyl.

18. A compound according to claim 1, wherein
R is a butyl-4,5-dihydro-4-oxo-5-$R^3$-3H-imidazo[4,5-c]-pyridin-3-yl,
$R^2$ is tetrazol-5-yl,
R is 3,3-dimethyl-2-oxobutyl, phenacyl, 2-(benzofuran2-oxoethyl or thien-2-yl-methyl, and
X is absent.

19. A pharmaceutical composition comprising a pharmaceutically acceptable carrier and a compound of claim 1.

20. A pharmaceutical composition according to claim 19, wherein said compound is present in an amount of 1 mg-1 g.

21. A method of treating or prophylaxis of angiotensin II-dependent diseases or conditions, comprising administering a compound according to claim 1.

22. A method according to claim 21, wherein said compound is administered in a daily dosage of 0.1-50 mg/kg.

23. A method according to claim 21, wherein said disease is angiotensin II-dependent hypertension.

24. A method according to claim 22, wherein said disease is angiotensin II-dependent hypertension.

* * * * *